United States Patent
Nelms

(10) Patent No.: US 9,463,336 B2
(45) Date of Patent: Oct. 11, 2016

(54) BENCHMARK SYSTEM FOR RADIATION THERAPY PLANNING

(71) Applicant: Sun Nuclear Corporation, Melbourne, FL (US)

(72) Inventor: Benjamin E. Nelms, Merrimac, WI (US)

(73) Assignee: Sun Nuclear Corporation, Melbourne, FL (US)

( * ) Notice: Subject to any disclaimer, the term of this patent is extended or adjusted under 35 U.S.C. 154(b) by 45 days.

(21) Appl. No.: 14/051,752

(22) Filed: Oct. 11, 2013

(65) Prior Publication Data

US 2015/0087879 A1    Mar. 26, 2015

Related U.S. Application Data

(60) Provisional application No. 61/880,387, filed on Sep. 20, 2013.

(51) Int. Cl.
*A61B 5/00* (2006.01)
*A61B 6/00* (2006.01)
*A61N 5/10* (2006.01)

(52) U.S. Cl.
CPC ............ *A61N 5/1071* (2013.01); *A61B 6/5294* (2013.01); *A61N 5/103* (2013.01); *A61N 5/1031* (2013.01); *A61N 5/1048* (2013.01); *A61N 5/1075* (2013.01); *A61B 6/50* (2013.01); *A61B 6/58* (2013.01); *A61N 2005/1041* (2013.01)

(58) Field of Classification Search
CPC ............ A61B 6/00; A61B 6/48; A61B 6/50; A61B 6/52; A61B 6/5294; A61B 6/58; A61N 5/00; A61N 5/10; A61N 5/103; A61N 5/1031; A61N 5/1048; A61N 5/1071; A61N 5/1075
USPC .............. 378/64, 65, 91, 162, 165, 210, 901
See application file for complete search history.

(56) References Cited

U.S. PATENT DOCUMENTS

| 8,130,905 B1 * | 3/2012 | Nelms .............................. 378/65 |
| 2005/0111621 A1 * | 5/2005 | Riker et al. ...................... 378/65 |

* cited by examiner

*Primary Examiner* — Anastasia Midkiff
(74) *Attorney, Agent, or Firm* — Mintz Levin Cohn Ferris Glovsky and Popeo, P.C.

(57) ABSTRACT

A system for evaluating radiation treatment planning generates a fictitious treatment dose matrix with a quality of dose placement beyond that achievable with physically realizable radiation therapy machines. Such a fictitious treatment dose matrix provides an objective measure that is readily tailored to different clinical situations, and although unattainable, thereby provides a benchmark allowing evaluation of radiation plan goals and the radiation plans between different multiple clinical situations and individuals.

19 Claims, 4 Drawing Sheets

| GOAL CATEGORY | GOAL VALUE | BENCHMARK | GUIDANCE | DETAILS |
|---|---|---|---|---|
| BOWEL MAX DOSE | ≤50GY | 45 | ACHIEVABLE | 1.00 |
| BLADDER V 35 Gy % | ≤5GY | 2.6902 | CHALLENGING | 0.046 |
| GENITALIA_EXT V 40 Gy % | ≤2GY | 1.6521 | DIFFICULT | 0.07 |
| RECTUM V 30 Gy % | ≤0.00GY | 0.1610 | POTENTIALLY IMPOSSIBLE | 0 |
|  |  |  |  |  |

FIG. 5

BENCHMARK SYSTEM FOR RADIATION THERAPY PLANNING

CROSS-REFERENCE TO RELATED APPLICATION

This application claims the benefit of U.S. Provisional Application Ser. No. 61/880,387 filed on Sep. 20, 2013 and hereby incorporated by reference.

BACKGROUND OF THE INVENTION

The present invention relates to medical radiation therapy and in particular to an electronic computer program for evaluating radiation therapy plans in light of unique patient anatomy and specific plan objectives.

Medical equipment for radiation therapy treats tumorous tissue with high-energy radiation. The amount of radiation and its placement must be accurately controlled to ensure both that the tumor receives sufficient radiation to be eradicated, and that the damage to the surrounding and adjacent non-tumorous tissue is minimized, with the goal of remaining under biological tolerance levels.

In external beam radiation therapy, a radiation source external to the patient treats internal tumors. The external source is normally collimated to direct a beam only to the tumorous site and often modulated with complex dose patterns. The source of high-energy radiation may be x-rays, or electrons from linear accelerators in the range of 2-25 MeV, or gamma rays from highly focused radioisotopes such as a $Co^{60}$ source having an energy of 1.25 MeV.

Typically, the tumor will be treated from a multitude of geometric directions with the intensity and shape of the beam adjusted appropriately. The purpose of using multiple beams which converge on the site of the tumor is to reduce the dose to areas of surrounding non-tumorous tissue. The angles at which the tumor is irradiated are selected to avoid angles which would result in irradiation of particularly sensitive structures near the tumor site. The angles and intensities of the beams for a particular tumor form a treatment plan for that tumor, with the ultimate goal to generate a three-dimensional (3D) dose that, in sum over all beams, conforms to the target volume(s) and spares healthy tissue One highly accurate method of controlling the dose to a patient termed intensity modulated radiation therapy (IMRT) employs a radiation source that is segmented with many individual apertures (usually formed by a multi-leaf collimator, or MLC) which in sum produce a complex modulated pattern specific to the anatomy and beam angle. IMRT beams maybe irradiate the patient from many beam angles, or can be delivered while the beam rotates about the patient such as with volume-modulated arc therapy (VMAT) or tomotherapy. U.S. Pat. No. 5,317,616, hereby incorporated by reference, describes the construction of one such machine and one method of calculating the necessary beam intensities as a function of angle.

The control of the radiation therapy machine during a treatment session or multiple treatment sessions is described by a radiation therapy plan developed by one or more healthcare professionals. The treatment plan normally begins a series of treatment goals, for example, defining minimum and maximum dose amounts for particular tissue volumes (called regions of interest, or ROI's), dose homogeneity and the extent to which the dose conforms to the defined ROI. The goals offer leeway in the trade-off between the competing objectives of delivering large doses to diseased tissue while minimizing doses to surrounding healthy tissue. Generally this trade-off exists because of an inability to precisely control radiation falloff at the boundary between healthy and diseased tissue caused by the physics of radiation scattering, and the need for the radiation to pass through healthy tissue on the way to or from the treated tissue.

The goals are used to guide the development of a radiation therapy plan describing, among other parameters, the type of radiation to be used, the orientation of the radiation therapy beams to be directed toward patient at multiple beam stations, the shape for collimation of the beams, and the amount of dose to be delivered at each station. In modern radiation treatment planning, the plan is often generated by the computer via a process called "inverse planning" or dose optimization.

The wide variety of different clinical situations presented by patients (e.g. varying anatomy size, shape, and location) prevents practical reuse of standard radiation plans but instead normally requires a custom radiation therapy plan be developed for each clinical situation. While there are computerized systems that can assist in the development of a clinical radiation therapy plan, the complexity of this process means that clinical radiation therapy plans for most important clinical situations require substantial input from a skilled human planner. Automated systems for developing clinical radiation therapy plans are frequently ineffective when one or more treatment goal is physically unattainable in a particular clinical situation or with a particular radiation therapy machine.

The practical uniqueness of each clinical situation and the wide variation in difficulty presented by each clinical situation make it extremely difficult to assess the quality of a given radiation therapy plan. While periodic contests among radiation therapy planners indicate a significant range in the quality of the plans produced, outside of the contest the individual planner has very little guidance with respect to how well his or her plan achieved the goals relative to other possible plans. See generally, Nelms, Benjamin E. et al., "Variation in external beam treatment plan quality: An inter-institutional study of planners and planning systems", Practical Radiation Oncology, vol. 2, issue 4, October-December 2012, pgs. 296-305, hereby incorporated by reference.

A simple comparison of a plan against the radiation plan goals on which the clinical radiation therapy plan is founded fails to provide the necessary guidance because failure to meet a radiation plan goal can simply reflect an improperly set plan goal or inherent difficulty in the particular clinical situation (for example, where there is a large overlap between healthy and diseased tissue). Even with all else equal—such as planning equipment, processes, technique, goals, and treatment planner—the degree to which the plan meets all the goals will vary, based solely on the unique anatomical challenges of each patient combined with physical limitations of dose deposition of radiation in the human body.

SUMMARY OF THE INVENTION

The present invention provides a useful and quantitative benchmark for the radiation therapy plan quality despite wide the variation in clinical situations which would otherwise appear to preclude meaningful comparisons or evaluation. In particular, the present invention creates a "fictitious" radiation dose matrix based on a simplified modeling of some of the radiation planning data for the clinical situation along with the limits of physics. Significantly, the model produces a highly conformal dose matrix that may be beyond (i.e. more conformal than) that attainable with actual radiation therapy equipment. Nevertheless, the fictitious radiation dose matrix reflects the underlying clinical situation in a way that allows the generation of a benchmark suitable for evaluation of the radiation plan goals before planning and for evaluation of the radiation plan after planning with reduced influence by the difficulty of the clinical situation or the particular radiation therapy goals set.

The fictitious radiation dose matrix may be compared against the radiation plan goals to quickly identify impossible goal values and/or to grade the goal categories according to how difficult they will be to achieve in the particular clinical situation. This grading permits constructive dialogue between the healthcare professionals setting the goals and those implementing the radiation treatment plan at an early stage in the process before significant time is invested. For example, the treatment planner can advise the physician who set the goals about any goals that cannot be physically achieved, and together they can negotiate trade-offs, either in target dose coverage or in healthy tissue dose levels.

The fictitious radiation dose may also be used to evaluate the ultimate clinical radiation therapy plan developed under the radiation plan goals by comparing the dose matrix produced by the clinical radiation therapy plan to the fictitious radiation dose matrix. Unlike an evaluation of a clinical radiation therapy plan against the goal values of the radiation plan goals, which can penalize a clinical radiation therapy plan if the goal values are unrealistic and/or if the specific patient anatomy presents unique challenges, the dynamic benchmark of the fictitious radiation dose provides a measure that is largely indifferent to the quantitative goal values. Because the dynamic benchmark of the fictitious radiation dose reflects the difficulty of the clinical situation by incorporating, a priori, the anatomy volumes' sizes, shapes, and locations, this benchmarking has relevance between different clinical situations as a general measure of radiation plan quality. That is, the plan quality for "Patient A" can be compared to that of a population of other patient plans that were designed with the same protocol of dose objectives.

Specifically then, in one embodiment, the present invention provides an evaluation system for radiation therapy operating on an electronic computer to receive a subset of radiation planning data for a given patient selected from the set of: anatomic volumes generated by drawn "contours" and treatment volume dose prescriptions. This subset of radiation planning data is used to generate a fictitious treatment dose matrix that overlaps the anatomic volumes, both target and healthy tissue. An electronic computer may then receive radiation planning information selected from the group consisting of radiation plan goals for the given patient and a clinical radiation therapy plan for the given patient and then evaluate the radiation planning information against the fictitious treatment dose matrix.

It is thus a feature of at least one embodiment of the invention to provide an objective benchmark for evaluating the radiation therapy planning process through a fictitious treatment dose matrix that may be objectively and automatically generated.

The subset and the modeling process may be selected so that the fictitious treatment dose matrix provides a quality of dose placement beyond that achievable with a physically realizable radiation therapy machine;

It is thus a feature of at least one embodiment of the invention to provide a benchmark that clearly provides a basis to evaluate impossible achievement and that provides a long-lived standard that can maintain consistency irrespective of advances in automatic dose planning.

The evaluation may provide a quantitative comparison of the radiation planning information against the fictitious treatment dose matrix. It is thus a feature of at least one embodiment of the invention to permit a relative evaluation of strengths and shortcomings of goals or treatment plan.

While an automated planning routine could be used to establish an automatic benchmark against human efforts, employing a fictitious treatment dose matrix that is beyond that achievable with physically realizable radiation therapy machines provides a standard that can maintain consistency irrespective of advances in automatic dose planning.

The subset of radiation planning data may include only anatomy volume contours and target volume prescriptions.

It is thus a feature of at least one embodiment of the invention to provide a model that receives fundamental information about the clinical situation addressed by the radiation planning process so that the benchmark of the fictitious treatment dose matrix properly reflects variations in the difficulty presented by the clinical situation.

The radiation planning information may be radiation plan goals that include evaluating the fictitious treatment dose matrix against the radiation plan goals to indicate a difficulty of attaining the radiation plan goals.

It is thus a feature of at least one embodiment of the invention to provide a way of assessing possibly unrealistic plan goals early in the process stage, before planning is undertaken and planning effort wasted.

The evaluation may indicate the probable impossibility of attaining at least a portion of the radiation plan goals, for example, when the goals that exceed the fictitious treatment dose matrix are indicated to be impossible.

It is thus a feature of at least one embodiment of the invention to provide a simple method of identifying impossible plan goals.

The evaluation may further indicate a range of multiple levels of difficulty between attainable and probably impossible for different portions of the radiation plan goals.

It is thus a feature of at least one embodiment of the invention to provide a more nuanced evaluation of plan goals that may lead to constructive assessment of the plan goals before radiation therapy planning.

In this regard, the program may include empirical data providing a histogram of degrees of goal attainment for human dose planners for given goal categories and the multiple levels of difficulty for each goal category may be based on the histogram for the corresponding goal category referenced against the evaluation of the fictitious treatment dose matrix against the goal category.

It is thus a feature of at least one embodiment of the invention to provide gradations in the assessment of difficulties of different goals commensurate with a scale of actual achievement of real human planners and treatment planning systems (TPS).

The radiation plan goals may include goal categories and goal values and the goal categories may be selected from the group of maximum dose to healthy tissue regions, minimum dose to treated tissue regions, treatment homogeneity, and treatment conformation.

It is thus a feature of at least one embodiment of the invention to provide an evaluation system that flexibly works with a variety of general and useful goals.

The output may provide a table separately displaying the radiation plan goals and an assessment of the difficulty of attaining that goal based on the fictitious treatment dose matrix.

It is thus a feature of at least one embodiment of the invention to provide a simple output reflecting the results of the benchmarking process.

The subset and the modeling process may be selected so that the fictitious treatment dose matrix provides a dose gradient no greater than that resulting from Compton scattering.

It is thus a feature of at least one embodiment of the invention to provide a fictitious treatment dose matrix that is superior, but not too far beyond, the best possible physical dose delivery, so as to provide an invariable benchmarking reference that provides a sensitive measure.

In one embodiment, the radiation planning information may be a clinical radiation therapy plan for the given individual and the method may include the step of evaluating the fictitious radiation dose matrix vs. the achieved clinical dose matrix of the clinical radiation therapy plan in terms of common radiation plan metrics, and the evaluation may compare the extents to which the clinical radiation therapy plan achieves the radiation plan goals relative to the same metrics resulting from the fictitious dose matrix.

It is thus a feature of at least one embodiment of the invention to provide an absolute evaluation of a clinical radiation therapy plan that may be used in a variety of clinical situations to assess and compare the quality of radiation plans.

The extent to which the fictitious radiation dose matrix and the clinical dose matrix of the clinical radiation therapy plan achieve different radiation plan metrics may be combined into a single evaluation for the clinical radiation therapy plan.

It is thus a feature of at least one embodiment of the invention to provide a single measure reflecting the quality of a clinical radiation therapy plan suitable for comparison to other clinical radiation therapy plans.

These particular features and advantages may apply to only some embodiments falling within the claims and thus do not define the scope of the invention.

BRIEF DESCRIPTION OF THE DRAWINGS

FIG. 5 is a fragmentary view of an output goal report using the fictitious treatment dose matrix to assess practicality of treatment goals;

DETAILED DESCRIPTION OF THE PREFERRED EMBODIMENT

Figure 1:
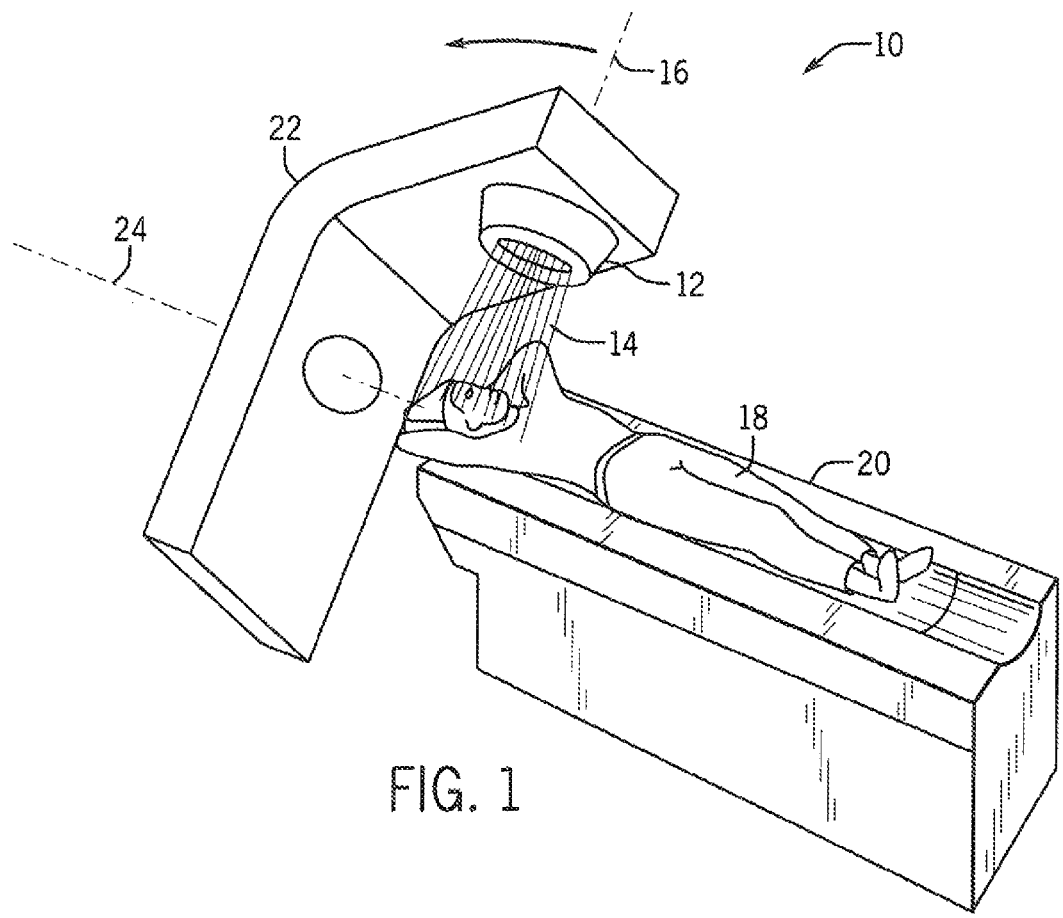
FIG. 1 is a simplified perspective view of a radiation therapy machine showing some of the parameters of radiation treatment control by radiation planning data.

Referring now to FIG. 1, a radiation therapy machine 10 may provide, for example, a radiation head 12 projecting one or more intensity control radiation beams 14 along an axis 16 toward a patient 18. The patient may be supported on a table 20 that may be translated and rotated to change the position of the patient 18 with respect to the beams 14. In addition, the radiation head 12 may be mounted on a rotatable gantry 22 rotatable about an axis 24 to move axis 16 to direct the radiation beam 14 at a variety of angles with respect to the patient 18. The radiation head 12 may include an internal collimator or multi-leaf collimator to controlled either or both of the outline or shape of the radiation beam 14 in cross-section and the intensity of all or portions of the radiation beam 14.

The treatment planning process, in its simplest expression, produces a clinical radiation therapy plan defining a set of stations at which the radiation beam 14 will be applied to the patient 18 wherein each station is defined by angles of the axis 16 and positions of the table 20 and a duration and/or intensities of the radiation beam 14 or portions of the radiation beam 14 at those different stations. Implicit in the data describing the clinical radiation therapy plan 75 may be information about the radiation therapy machine 10 and the type of radiation produced. The positions of the table 20 and the axis 16 are normally reference with respect to particular tissues or organs of the patient 18. The data capturing the clinical radiation therapy plan 75 may be contained in a computer file used to control the radiation therapy machine 10, for example, a DICOM RT file as is generally understood in the art.

Figure 2:
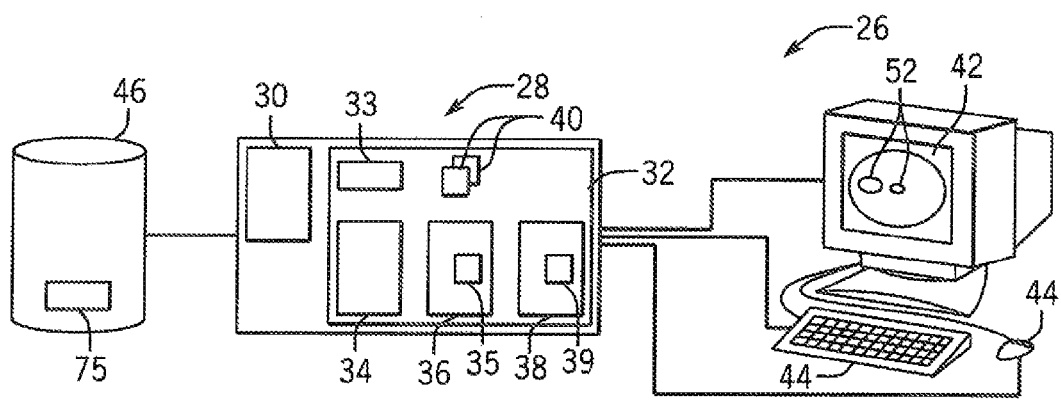
FIG. 2 is a simplified block diagram of an electronic computer suitable for execution of the program of the present invention.

Referring now to FIG. 2, the process of preparing a clinical radiation therapy plan may be performed on an electronic computer 26, for example, a desktop computer system. The electronic computer 26 may include a processing unit 28 incorporating one or more processors 30 and electronic memory 32 in communication with the processors 30. Electronic memory 32 may store in non-transient media, an operating system 34 (e.g. the Windows operating system) treatment planning software 36 of the type known in the art for developing a clinical dose matrix 35 as will be described, a treatment plan quality assessment system 33 of a type known in the art processing a given clinical radiation therapy plan, benchmarking software 38 of the present invention for generating a fictitious dose matrix 39, and empirically collected data 40 as will also be described below. The processing unit 28 may communicate with a standard graphic display 42 and user input devices 44 (such as a mouse and keyboard) and may communicate with a remote data storage device 46, for example, to provide for inputs of 3-D image data and the like.

Figure 3:
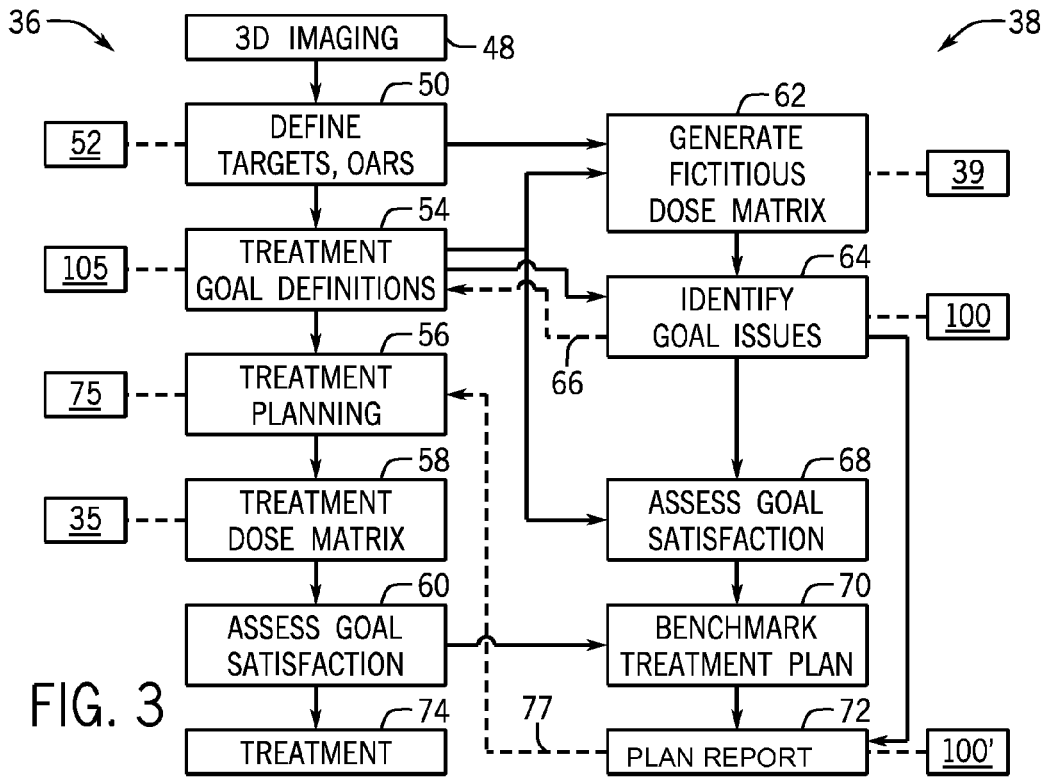
FIG. 3 is a flowchart showing the process of preparing a radiation treatment plan including steps executable on the computer of FIG. 2.

Referring now to FIGS. 2 and 3, a typical treatment planning process using the computer 26 of FIG. 2 may begin with the acquisition of three-dimensional imaging data as indicated by process block 48. Such imaging data may be obtained, for example, with any of a variety of imaging modalities, for example computed tomography (CT), PET imaging, MRI and the like, and will typically provide data sufficient to present one or more cross-sections (slices) together representing a three-dimensional volume of the patient in a region of interest (ROI) to be treated by the radiation beams 14.

As indicated by process block 50, this data may be presented on the display 42 by the treatment planning software 36 to allow the radiation target and surrounding organs at risk (OARS) to be contoured, for example, by being circumscribed in multiple cross-sectional regions with contours 52. This process may be done by manual control of the cursor guided by visual inspection through the user input devices 44 as augmented by automatic contouring programs known in the art. Generally the contours 52 need not be associated with an individual organ but may represent therapeutic regions.

At process block 54, radiation plan goals may be defined related to individual or multiple of the contours 52. Such radiation plan goals may include, for example, a minimum desired dose for the region of the contour (typically for diseased tissue to be treated), a maximum desired dose for the region of the contour (typically for healthy surrounding tissue and organs at risk) and varied statistical goals such as dose homogeneity and dose conformance, as will be discussed further below.

Based on the defined contours 52 of process block 50 and the radiation plan goals of process block 54, treatment planning may be undertaken using the treatment planning software 36 as indicated by process block 56. Generally this process involves an interactive process of selection by a clinician of various stations for the radiation therapy machine 10 and the desired beam intensity and duration. An internal modeling is then conducted, as will be described in more detail below, to produce a clinical dose matrix 35 per process block 58 providing an indication of the actual dose received by the tissue in the region of interest using the treatment plan developed at process block 56 applied to actual radiation therapy machine 10.

At process block 60, the clinical dose matrix 35 of process block 58 may be compared against the radiation therapy goals 105 defined at process block 54 to indicate the extent to which the radiation therapy goals 105 have been satisfied by the produced clinical dose matrix 35. Depending on the outcome of this assessment, process blocks 56 and 58 may be repeated until a desired clinical dose matrix 35 is obtained.

The steps of process blocks 50, 54, 56, and 58 may be performed by treatment planning software 36 from a variety of commercial sources including, for example, "Eclipse" commercially available from Varian Medical Systems (Palo Alto, Calif.). The assessment of the goal satisfaction of process block 60 may be performed by a treatment plan quality assessment system 33 such as "Quality Reports [EMR]" commercially available from Canis Lupus LLC, Merrimac, Wis., USA.

Referring still to FIGS. 2 and 3, the benchmarking software 38 may receive the defined contours 52 of targets and organs at risk from process block 50 and the treatment goals of process block 54 (or this data may be entered separately) to generate a fictitious dose matrix 39 as indicated by process block 62. This fictitious dose matrix 39, as will be discussed below, is calculated to provide for a dose placement on the patient tissues within the ROI that is superior to any physically realizable dose placement, and maybe obtained, for example, by relaxing and simplifying the constraints that normally attend to modeling a clinical dose matrix. Although the fictitious dose matrix 39 cannot be achieved in reality, it is nevertheless based on the specific data about the patient's unique anatomy and target volume dose prescription and OAR dose objectives concurrently provided as inputs to the treatment planning software 36 and thus generally will provide an benchmark adjusted to the actual treatment plan and the particular clinical situation presented by the patient 18. Thus, for clinical situations where patient anatomy makes it difficult to realize the desired treatment goals 105, the fictitious dose matrix 39 will present a fictitious dose matrix 39 of lower quality and thus a lower benchmark than for clinical situations where patient anatomy makes it easier to realize desired goals. This is similar to "grading on a curve" the plan quality on a per-patient plan basis.

While the fictitious dose matrix 39 cannot be implemented in reality, it provides two useful benchmarking functions. First, indicated by process block 64, before the treatment planning of process block 56 has begun, the fictitious dose matrix 39 may be applied to the radiation therapy goals 105 of process block 54 to identify those radiation therapy goals 105 that will be difficult to attain. Generally, radiation therapy goals 105 that cannot be met by the fictitious dose matrix 39 will be impossible to attain. The fictitious dose matrix 39 may further be used to indicate attainable but difficult goals. The results of this analysis may be provided in the goal report 100 as will be described below. Based on the outcome of process block 64, treatment goals at process block 54 may be revised as indicated by dotted arrow 66.

Second, fictitious dose matrix 39 of process block 62 may also be used to assess the clinical, i.e. achieved, dose matrix 35 and hence the treatment plan developed at process block 58 generated by the treatment planning software 36. In this case, the fictitious dose matrix 39 of process block 62 is assessed against the radiation therapy goals 105 of process block 54 at process block 68. At process blocks 70, this assessment of the fictitious dose matrix 39 of process block 62 may then be compared to the assessment of the clinical dose matrix 35 developed at process block 60. This latter assessment of process block 70, based on the dynamic benchmark provided by the fictitious dose matrix 39 accommodates and compensates for the clinical situations presenting different levels of difficulty, allowing clinical treatment plans 75 for different patients to be more readily compared to each other and a given clinical treatment plan 75 to be assessed with respect to the practically absolute standard of the fictitious dose matrix 39. The results of this assessment of process block 70 may be output in a plan report 100' in process block 72 providing the components of the comparison and a distillation of the comparison to a single number as will be described below. The results of this plan report 100' may provoke a change in the treatment plan as indicated by arrow 77.

At the conclusion of the benchmarking process and possible iterations between benchmarking and treatment planning, a clinical treatment plan 75 is obtained and treatment provided as indicated by process block 74 typically producing one or more DICOM-RT files used to control the radiation therapy machine 10.

Figure 4A:
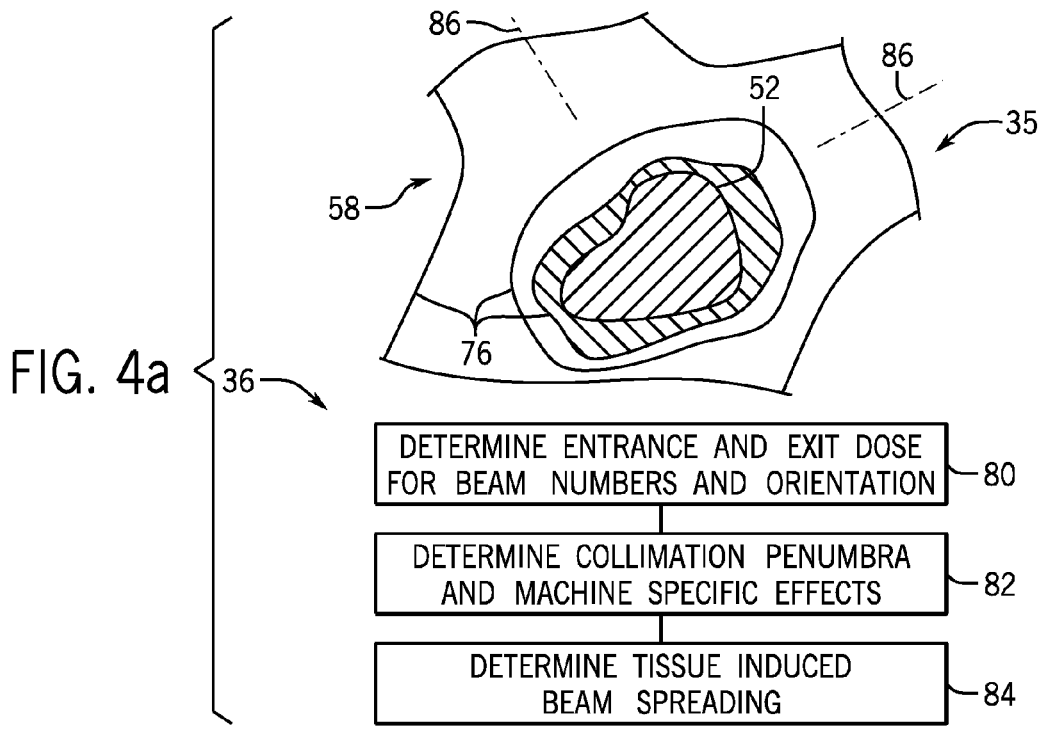
FIGS. 4a and 4b are figures showing simplified representations of a clinical dose matrix produced by a clinical radiation therapy plan and a fictitious treatment dose matrix, respectively, and showing steps for producing each.

Referring now to FIGS. 3 and 4a, a computerized modeling process used to produce the clinical dose matrix 35 per process block 58 takes a current iteration of the clinical treatment plan 75 of process block 56 and computes iso-dose lines 76, for example, as may be displayed on the display 42 with respect to a region of a contour 52. The iso-dose lines 76 represent the clinical dose matrix 35 indicating the dose that will be applied to the patient tissue in the region of interest. While a number of different modeling approaches may be taken by commercial treatment planning software 36, such modeling will typically account for all or most of the dose deposited by radiation sources defined in the treatment plan of process block 56 as indicated by process block 80. In addition, variations in the dose caused by physical limitations of the radiation therapy machine 10 such as a collimation penumbra or other machine specific effects such as energy spectra, collimator transmissions, MLC leaf end shapes, inter-leaf leakage, etc. may be accounted for as indicated by process block 82. In addition, geometric considerations such as the distance of the radiation head 12 from the tissue of the patient 18 and the amount of intervening tissue such as may affect scattering and beam spreading as well as local scattering caused by the physical process called Compton Scatter and the like may be accounted for in this model as indicated by process block 84. The effect of this sophisticated modeling is to accurately predict the 3D dose in the complex human density matrix approximated by a set of CT images. Accurate modeling is necessary to estimate the dose gradients near anatomy contours 52 suggested by separated iso-dose lines as well as to indicate significant radiation dose along the paths 86 of particular beams. The possible dose gradients will generally govern the trade-off between high-dose delivered to contour 52 of diseased tissue and low-dose delivered to external healthy tissue and may lower the ability of the underlying treatment plan 75 to achieve the radiation goals 105.

Figure 4B:
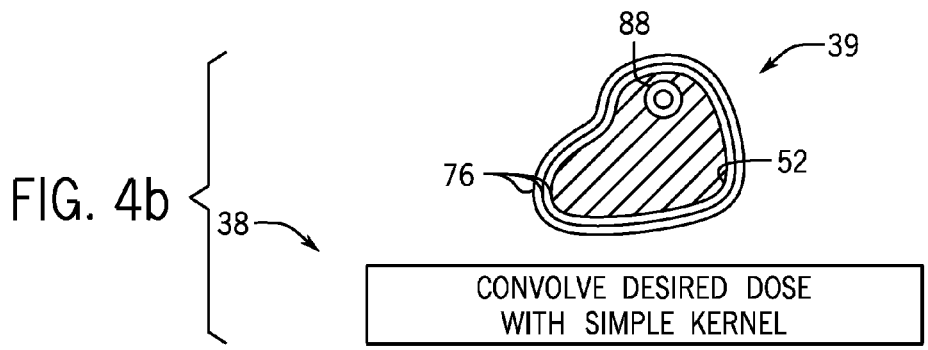

Referring now to FIGS. 3 and 4b, in contrast, the fictitious dose matrix 39 of process block 62 may use a much simpler modeling process intended to provide a fictitious dose matrix 39 superior to all attainable dose matrices. This is most simply obtained by neglecting one or more of the modeling effects described with respect to clinical dose matrix 35 that tend to decrease the dose gradient around the contour 52. In one embodiment, the fictitious dose matrix 39 is obtained by a simple and rapid dose gradient model that mathematically convolves the desired dose of the contour 52 with a scatter kernel 88, for example, representing lateral Compton scattering of dose, i.e. dose gradient normal to the beam axis, in human tissue absorbing radiation.

Such a convolution kernel can be empirical derived by sampling maximum observed dose gradients in the sharpest beam penumbra (or dose fall-off in the Bragg peak for proton beams) as a function of radiological depth in the patient. Generally, the fictitious dose matrix 39 will have iso-dose lines 76 that are closely spaced representing a steep falloff of radiation from the treated contour 52.

Referring now to FIGS. 3 and 5, the radiation plan goals 105 of process block 54, for example, indicated as various rows of an output goal report 100, may be assessed against the fictitious dose matrix 39 of FIG. 4b by analyzing goal values 102 against benchmark achieved goal values 104 provided by the fictitious dose matrix 39 for each plan goal 105. So, for example, a goal category 107 of the maximum dose in the bowel of less than or equal to 50 Gray per radiation plan goals 105a may be compared against the benchmark achieved goal values 104 in the bowel region by the fictitious dose matrix 39 to indicate that this goal should generally be achievable as indicated by qualitative difficulty value 106 of "achievable" capturing a quantitative difficulty value 108 underlying the qualitative difficulty value 106 calculated as will be discussed below.

In contrast, the goal category 107 of volume percent for the rectum of less than or equal to 0.001 Gray per radiation plan goals 105d may be compared against the benchmark achieved goal values 104 for volume percent dose obtained in the rectum by the fictitious dose matrix 39 to indicate that this goal is likely impossible as indicated by the qualitative difficulty value 106 for radiation plan goal 105d.

A variety of different quality radiation plan goals 105 may be established generally for each different treatment contour 52 including organs and "planning treatment volumes" (PTV) typically defined with respect to a tumor as indicated below in Table I. With respect to the above description, the maximum dose of radiation plan goals 105a is item number 7 and the volume percent of radiation plan goals 105d is item number 4 in the Table 1.

TABLE I

Radiation Plan Goals

| | Goal Category | Goal Value Unit | Description |
|---|---|---|---|
| 1 | DVH Dose-at-Percent-Volume | Gy | Dose value (Gy) at a given cumulative DVH percent volume (%) for a specified region of interest (ROI) |
| 2 | DVH Dose-at-Absolute-Volume | Gy | Dose value (Gy) at a given absolute DVH volume (cc) for a specified ROI |
| 3 | DVH Absolute-Volume-at-Dose | cc | Absolute volume (cc) at a given dose value (Gy) for a specified ROI |
| 4 | DVH Percent-Volume-at-Dose | % | Percent volume (%) at a given dose value (Gy) for a specified ROI |
| 5 | Min Dose | Gy | Minimum dose grid value inside a specified ROI |
| 6 | Mean Dose | Gy | Mean over all dose grid values inside a specified ROI |
| 7 | Max Dose | Gy | Maximum dose grid value inside a specified ROI |
| 8 | Global Max | Gy | Maximum dose grid value over all grid values |
| 9 | Global Max Location | — | Returns any/all ROIs that contain the global, max point |
| 10 | Serial Slice OAR Dose Evaluation | Pass/Fail | Determines the axial slices (if any) of a specified ROI (i.e. organ-at-risk) where all dose grid values in the plane(s) are greater than or equal to a specified threshold dose |
| 11 | High Dose Volume-of-Regret | cc | Volume (cc) outside of a specified target ROI volume that exceeds a specified threshold dose |
| 12 | Irradiated Volume | cc | Volume (cc) of any tissue receiving a dose of the specified threshold dose or more |
| 13 | Conformation Number (equivalent to RTOG Conformity Index) | — | (Volume (cc) of Specified ROI Covered by Specified Dose)/(Total Volume (cc) Covered By Specified Dose × Total ROI Volume) Ref: van't Riet et al. IJROBP 37(3), 731-736 |
| 14 | Conformality index | — | (Total Volume (Cc) Covered by Specified Dose)/(Total Target Volume (cc) Covered By Specified Dose × Total ROI Volume) Ref: Shaw et al. IJROBP, 27(5), 1231-1239 |
| 15 | Homogeneity Index | — | (Dose Covering 1% of ROI (Gy)-Dose Covering 99% of |

TABLE I-continued

Radiation Plan Goals

| Goal Category | Goal Value Unit | Description |
|---|---|---|
| 16 Inhomogeneity Index | — | ROI)/(ROI Prescription Dose (Gy)) Ref: Pezner et al. Radiotherapy and Oncology, 81(1), 81-35 (ROI Max Dose (Gy)-ROI Minimum Dose (Gy))/ROI Mean Dose (Gy) Ref: Tomé et al. IJROBP, 47(4), 1137-1143 |

In the above Table 1, (ROI) means region of interest, typically an organ or defined region, (DVH) means cumulative dose volume histogram, that is a histogram of the dose for each bin represents the number of volume elements of the region of interest achieving at least the given dose of the bin, and (Gy) means Gray, a unit of radiation dose.

Figure 6:
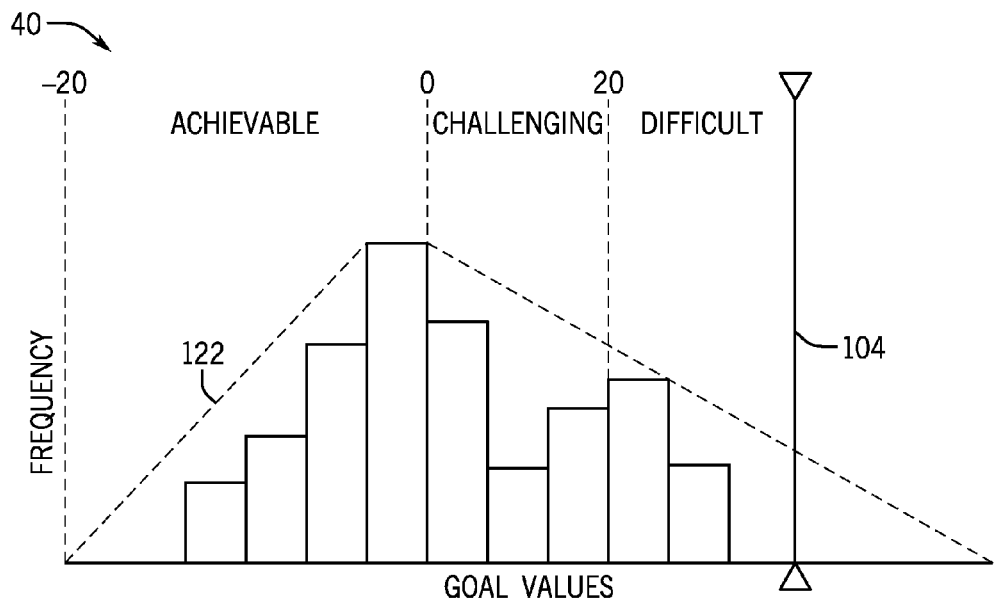
FIG. 6 is a representation of a histogram of actual attainment of treatment goals in a given corresponding goal category by human treatment planners as normalized by the fictitious treatment dose matrix to determine degrees of attainability of a particular treatment goal.

Referring now to FIGS. 5 and 6, the potentially impossible goals, for example, of radiation plan goals 105d are easily characterize by determining goal values 102 that exceed the benchmark achieved goal values 104 obtained by the fictitious dose matrix 39.

Nevertheless guidance of qualitative difficulty value 106 may also include various ranges of achievable goals below impossible ranked qualitatively as "achievable" (per radiation plan goals 105a), "challenging" (per radiation plan goal 105b) and "difficult" (per radiation plan goal 105c).

These non-impossible qualitative difficulty values 106 again are based on an underlying quantitative difficulty value 108 that may be determined using empirically collected data 40 representing the actual best efforts of human and/or automated radiation treatment planners in addressing that particular goal with respect to the same region of interest (e.g. the bowel, the bladder, etc.). This empirically collected data 40 may be expressed as a histogram of achievement of goal values and fit to a bell curve 122. In this histogram, the goal values achieved by each of the radiation planners are sorted into bins per ranges of achieved goal values to provide measures of frequency at which a given range of goal values is achieved. The bell curve 122 may be offset along the horizontal axis until the second sigma point (−2σ) of the bell curve 122 above the mean matches the benchmark value 104 of the fictitious dose matrix 39 for that particular plan goal 105. A qualitative difficulty value 106 of "achievable" may be awarded for goal values 102 of the clinical dose matrix 35 for particular plan goal 105 that fall within a range defined by the first two sigma values below the mean of the adjusted bell curve 122. Quantitative difficulty values 106 of "challenging" may be awarded for goal values 102 values that fall between the mean and the first sigma point above the mean, and quantitative difficulty values 106 of "difficult" may be those that fall between the first sigma point above the mean and the second signal point above the mean. As noted before, quantitative difficulty values 106 of "impossible" are goal values one or two above benchmark achieved goal values 104 of the fictitious dose matrix 39.

The table of FIG. 5 maybe output for use by the user as indicated by process block 72 of FIG. 3.

Figure 7:
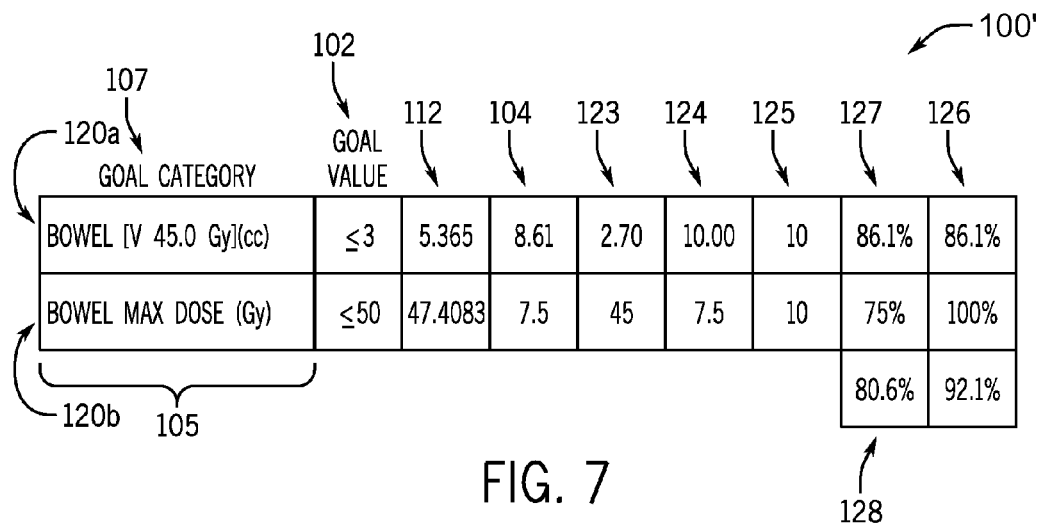
FIG. 7 is a fragmentary view of an output plan report assessing the quality of a clinical radiation treatment plan against a benchmark of the fictitious treatment dose matrix.

Referring now to FIG. 7, the present invention may be used not only to evaluate the achievability of the radiation plan goals 105 per process block 54 but also to absolutely benchmark the resulting clinical dose matrix 35 of process block 58 and hence the radiation therapy plan 75 of process block 56 in a way that compensates for the varying difficulty of the particular clinical situation. This characterization may be according to metrics which may follow the formula of the plan goals 105 while mapping the achievement under that formula to an absolute scale, for example from 0 to 10. Thus, for example, a goal of Max Dose to the spine (7 in Table I above) might map dose values to score values according to a function that provides 10 points for dose is less than 30 Gy, zero points for dose is greater than 50 Gy with the score interpolated linearly between these limits. A spine maximum dose value of 40 Gy would then mapped to a score value of 5 and a spine dose value of 35 Gy would then mapped to a score value of 7.5. This mapping is predetermined and arbitrarily adjusted so that the range of 0 to 10 fully embraces possible goal achievement.

This characterization of the clinical dose matrix 35 differs from the evaluation described above with respect to FIG. 5 in that it doesn't provide an indication of the achievability of the plan goal 105 but instead an indication of how effective the planner was independent of the achievability of the plan goals 105.

For this purpose, the goal value 102 is ignored and the clinical goal realization value 112 actually realized by the treatment dose matrix of process block 58 according to the goal category 107 for each radiation plan goal 105 quantitatively compared against the benchmark achieved goal values 104 of the fictitious dose matrix 39. This comparison may, for example, simply divide the score values, computed as discussed above, of the clinical dose matrix by the fictitious dose matrix. Assuming, for a particular region such as the spine, that the clinical dose matrix provides a Max Dose value of 40 Gy and the fictitious dose matrix provides a Max Dose value of 35 Gy, the comparison would compute a score value of 5/7.5 or 66.7 percent, normalized to be 6.67 out of 10. This process inherently normalizes the actual clinical scoring by the difficulty of the clinical challenge is as reflected in the scoring of the fictitious dose matrix.

In this example of FIG. 7, the clinical goal realization value 112 of 5.365 for radiation plan goals 120a (corresponding generally to a corresponding goal of a radiation plan goals 105 of FIG. 5) produces a goal score 104 of 8.61. The goal realization value 123 of 2.70 of the fictitious dose map, in contrast, produces a goal score 124 of 10 out of a maximum score 125 of 10. Comparing these two goal scores 104 and 124 provides a performance ranking 126 of 86.1%. Note that this high performance ranking 126 is despite the fact that this was a challenging goal value 102, an accommodation intrinsic to the referencing of the clinical goal realization value 112 against the benchmark value 104 of the fictitious dose matrix 39 rather than against the goal values 102 themselves.

In a second example, the clinical goal realization value 112 of 47.4083 for radiation plan goals 120b produces a goal score 104 of 7.5. The goal realization value 123 of 45 of the fictitious dose map, in contrast, produces a goal score 7.5 of 10 out of a maximum score 125 of 10. Comparing these two goal scores 104 and 124 provides a performance ranking 126 of 100 percent %. Note that this 100 percent performance ranking is higher than the 75 percent unadjusted value 127 that would be obtained from goal score 104 alone.

Each of these performance rankings 126 may be combined (for example by straight or weighted averaging) to provide a total plan ranking 128 (or total plan score) for the entire plan 75. This total plan ranking 128 may, for example, be reasonably compared against total plan ranking 128 for other clinical situations, even those clinical situations relate to different patients and even different organs. In addition, the total plan ranking 128 may provide some basis for performance measurements between individuals even working on different clinical situations. The plan report 100' of FIG. 7 may be output as indicated by process block 72 of FIG. 3.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

The term "clinical dose matrix" indicates simply that the radiation therapy plan intended for use in a medical application. The term "fictitious" as used herein is intended only as shorthand for the benchmarking process and does not indicate any particular subjective qualities.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

References to "a microprocessor" and "a processor" or "the microprocessor" and "the processor," can be understood to include one or more microprocessors that can communicate in a stand-alone and/or a distributed environment(s), and can thus be configured to communicate via wired or wireless communications with other processors, where such one or more processor can be configured to operate on one or more processor-controlled devices that can be similar or different devices. Furthermore, references to memory, unless otherwise specified, can include one or more processor-readable and accessible memory elements and/or components that can be internal to the processor-controlled device, external to the processor-controlled device, and can be accessed via a wired or wireless network.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications are hereby incorporated herein by reference in their entireties.

What I claim is:

1. A system comprising:
    at least one programmable processor; and
    a non-transient machine-readable medium storing instructions which, when executed by the at least one programmable processor, cause the at least one programmable processor to perform operations comprising:
    (a) receive a subset of radiation planning data for a given patient selected from a set of: anatomy volume contours and target volume prescriptions;
    (b) generate a fictitious treatment dose matrix from the subset of radiation planning data with a modeling process wherein the subset and the modeling process are selected so that the fictitious treatment dose matrix provides a quality of dose placement beyond that achievable with a physically realizable radiation therapy machine;
    (c) receive radiation planning information selected from the group consisting of radiation plan goals for the given patient and a clinical radiation therapy plan for the given patient;
    (d) evaluate the radiation planning information against the fictitious treatment dose matrix; and
    (e) output the evaluation.

2. The system of claim 1 wherein the evaluation provides a quantitative comparison of the radiation planning information against the fictitious treatment dose matrix.

3. The system of claim 1 wherein the subset of radiation planning data is only anatomy volume contours and target volume prescriptions.

4. The system of claim 1 wherein the radiation planning information is radiation plan goals and further including the step of evaluating the fictitious treatment dose matrix against goal values of the radiation plan goals to indicate a difficulty of attaining the radiation plan goals.

5. The system of claim 4 wherein the evaluation indicates probable impossibility of attaining at least a portion of the radiation plan goals.

6. The system of claim 5 wherein goal values of the radiation plan goals that exceed those obtained by the fictitious treatment dose matrix are indicated to be impossible.

7. The system of claim 4 wherein the evaluation indicates a range of multiple levels of difficulty between attainable and probably impossible for goal values of different portions of the radiation plan goals.

8. The system of claim 7 wherein the program includes empirical data providing a histogram of degrees of goal attainment for human dose planners for given goal categories and wherein the multiple levels of difficulty for each goal category are based on the histogram for a corresponding goal category referenced against the evaluation of the fictitious treatment dose matrix against the goal category.

9. The system of claim 4 wherein the radiation plan goals include goal categories and goal values and wherein the goal categories are selected from the group of maximum dose to healthy tissue regions, minimum dose to treated tissue regions, treatment homogeneity, and treatment conformation.

10. The system of claim 4 wherein the output provides a table separately displaying the radiation plan goals and an assessment of the difficulty of attaining the goal values of each goal based on the fictitious treatment dose matrix.

11. The system of claim 2 wherein the subset and the modeling process are selected so that the fictitious treatment dose matrix provides a dose gradient no greater than that resulting from Compton scattering.

12. The system of claim 1 wherein the quality of the fictitious treatment dose matrix is determined by at least one of a quantitative dose range, a quantitative conformance, and a quantitative dose homogeneity.

13. The system of claim 1 wherein the radiation planning information is a clinical radiation therapy plan for the given individual and including the step of evaluating the fictitious radiation dose matrix and a clinical dose matrix of the clinical radiation therapy plan against common radiation plan metrics and wherein the evaluation compares an extent to which the fictitious radiation plan and clinical radiation therapy plan achieve the radiation plan metrics.

14. The system of claim 13 including the step of the combining of comparisons of the extent to which the fictitious radiation dose matrix and the dose matrix of the clinical radiation therapy plan achieve different radiation plan metrics into a single evaluation for the clinical radiation therapy plan.

15. The system of claim 13 wherein the radiation plan metrics include metric categories and metric values and wherein the metric categories are selected from the group of maximum dose to healthy tissue regions, minimum dose to treated tissue regions, treatment homogeneity, and treatment conformation.

16. The system of claim 13 wherein output provides a table separately displaying the radiation plan metrics and an assessment of the clinical radiation therapy plan for each radiation plan metric.

17. A system comprising:
at least one programmable processor; and
a non-transient machine-readable medium storing instructions which, when executed by the at least one programmable processor, cause the at least one programmable processor to perform operations comprising:
  (a) receive a subset of radiation planning data for a given patient selected from a set of: anatomy volume contours and target volume prescriptions;
  (b) generate a fictitious treatment dose matrix from the subset of radiation planning data with a modeling process, wherein the subset and the modeling process are selected so that the fictitious treatment dose matrix provides a dose gradient no greater than that resulting from Compton scattering;
  (c) receive radiation planning information selected from the group consisting of radiation plan goals for the given patient and a clinical radiation therapy plan for the given patient;
  (d) evaluate the radiation planning information against the fictitious treatment dose matrix, wherein the evaluation provides a quantitative comparison of the radiation planning information against the fictitious treatment dose matrix; and
  (e) output the evaluation.

18. A system comprising:
at least one programmable processor; and
a non-transient machine-readable medium storing instructions which, when executed by the at least one programmable processor, cause the at least one programmable processor to perform operations comprising:
  (a) receive a subset of radiation planning data for a given patient selected from a set of: anatomy volume contours and target volume prescriptions;
  (b) generate a fictitious treatment dose matrix from the subset of radiation planning data with a modeling process;
  (c) receive radiation planning information selected from the group consisting of radiation plan goals for the given patient and a clinical radiation therapy plan for the given patient, wherein the radiation planning information is radiation plan goals;
  (d) evaluate the radiation planning information against the fictitious treatment dose matrix, wherein the evaluation indicates probable impossibility of attaining at least a portion of the radiation plan goals;
  (e) evaluate the fictitious treatment dose matrix against goal values of the radiation plan goals to indicate a difficulty of attaining the radiation plan goals; and
  (f) output the evaluation.

19. The system of claim 18 wherein goal values of the radiation plan goals that exceed those obtained by the fictitious treatment dose matrix are indicated to be impossible.

* * * * *